(12) United States Patent
Pallia

(10) Patent No.: US 9,301,832 B2
(45) Date of Patent: Apr. 5, 2016

(54) TENDON ANCHOR AND METHOD OF USING SAME

(71) Applicant: Christopher Sterling Pallia, San Diego, CA (US)

(72) Inventor: Christopher Sterling Pallia, San Diego, CA (US)

(*) Notice: Subject to any disclaimer, the term of this patent is extended or adjusted under 35 U.S.C. 154(b) by 205 days.

(21) Appl. No.: 13/956,743

(22) Filed: Aug. 1, 2013

(65) Prior Publication Data

US 2015/0038998 A1 Feb. 5, 2015

(51) Int. Cl.
*A61B 17/08* (2006.01)
*A61F 2/08* (2006.01)

(52) U.S. Cl.
CPC ....... *A61F 2/0811* (2013.01); *A61F 2002/0829* (2013.01); *A61F 2002/0864* (2013.01)

(58) Field of Classification Search
CPC .......... A61B 17/8645; A61B 2017/0414; A61B 2017/0427; A61B 2017/0429; A61B 2017/0459; A61B 2017/0464; A61F 2002/0829; A61F 2/0811; A61F 2002/0864; A61F 2002/087; A61F 2002/0882; A61F 2002/085
USPC ........... 606/151, 232, 327, 60, 323, 300, 301, 606/313; 623/13.14
See application file for complete search history.

(56) References Cited

U.S. PATENT DOCUMENTS

| | | | |
|---|---|---|---|
| 5,800,544 A * | 9/1998 | Demopulos et al. | 623/13.13 |
| 6,355,066 B1 | 3/2002 | Kim | |
| 6,645,227 B2 * | 11/2003 | Fallin et al. | 606/232 |
| 7,651,528 B2 | 1/2010 | Montgomery et al. | |
| 7,955,388 B2 | 6/2011 | Jensen et al. | |
| 7,967,861 B2 | 6/2011 | Montgomery et al. | |
| 8,048,158 B2 | 11/2011 | Hays et al. | |
| 8,147,546 B2 | 4/2012 | Stone et al. | |
| 2002/0161401 A1 * | 10/2002 | Steiner | A61B 17/0401 606/232 |
| 2008/0177386 A1 * | 7/2008 | Cerundolo | 623/13.14 |
| 2008/0228271 A1 * | 9/2008 | Stone et al. | 623/13.12 |
| 2010/0145448 A1 | 6/2010 | Montes De Oca Balderas | |
| 2012/0150296 A1 * | 6/2012 | Miller | 623/13.14 |
| 2012/0165868 A1 * | 6/2012 | Burkhart et al. | 606/232 |

OTHER PUBLICATIONS

"Treatment of Ankle Fractures Using New High-Strength, Bioactive, Biorsorbable Forged Composites of Unsintered Hydroxyapatite / poly-L-lactide (F-u-HA/PLLA) Implants," by Takada N. ,Suzuki H., Yamada K., Otsuka T., Published on Mar. 13, 2011 in Journal of Orthopaedics.

* cited by examiner

*Primary Examiner* — Katherine M Shi

(74) *Attorney, Agent, or Firm* — Jerry R. Potts; James R. McDaniel

(57) ABSTRACT

A tendon anchor, a housing, a protuberance located substantially on the housing, a cut-out area located substantially on the housing and located substantially across from the protuberance, and a plurality of elongated tendon gripping projections located substantially adjacent to the protuberance and the cut-out area for substantially retaining the tendon within the tendon anchor.

19 Claims, 10 Drawing Sheets

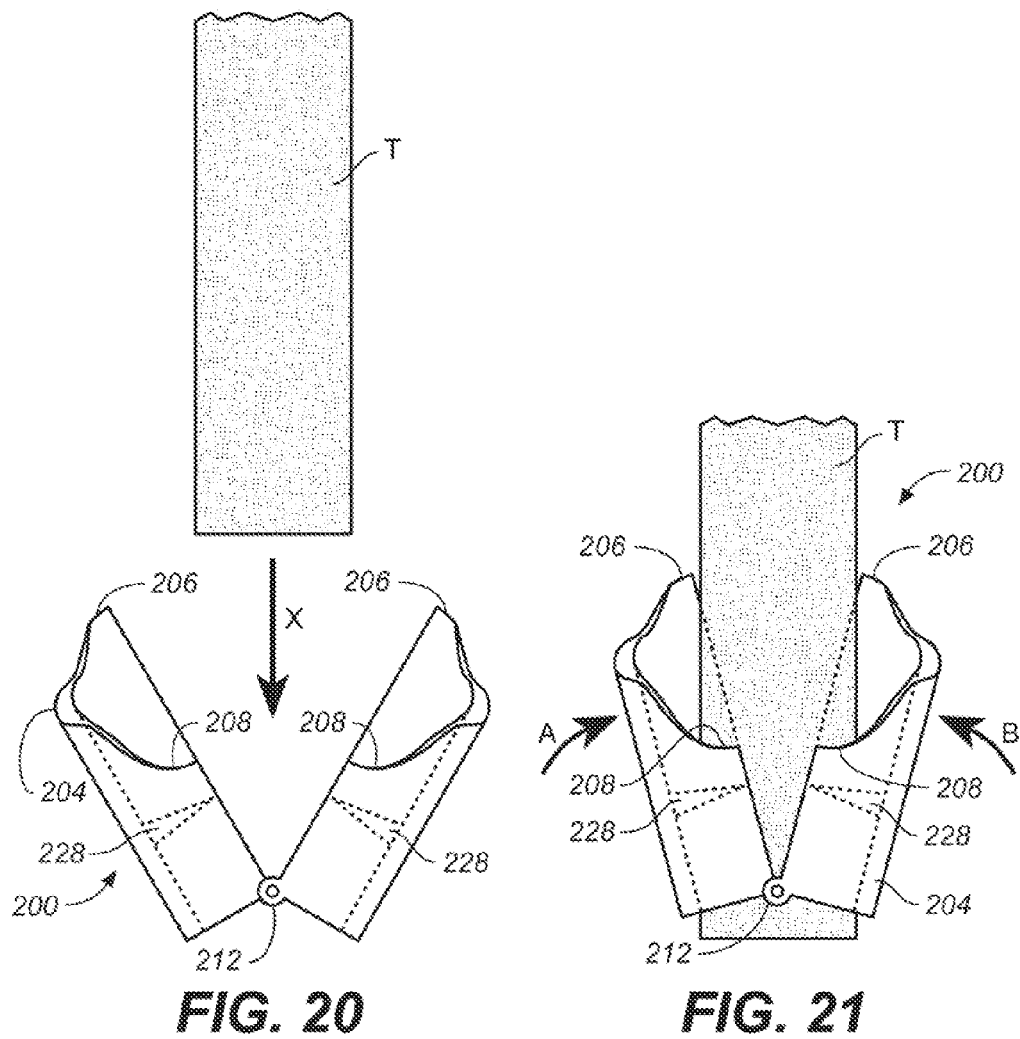

TENDON ANCHOR AND METHOD OF USING SAME

FIELD OF THE INVENTION

This invention relates generally to tendon anchors and more particularly to an attachment that can be applied to a tendon to anchor the tendon to the bone.

BACKGROUND OF THE INVENTION

Prior to the present invention, as set forth in general terms above and more specifically below, it is known, to use tendon anchors which include spikes. See for example, U.S. Pat. No. 8,147,546 to Stone, et al., U.S. Pat. No. 8,048,158 to Hays, et al. U.S. Pat. No. 7,967,861 to Montgomery, et al., U.S. Pat. No. 7,955,388 to Jensen, et al., U.S. Pat. No. 7,651,528 to Montgomery et al., U.S. Pat. No. 6,355,066 to Kim, U.S. Patent Application Publication No. 20120150296 to Miller, and U.S. Patent Application Publication No. 20100145448 to Montes de Oca Balderas. While the use of spikes in tendon anchors may have been generally satisfactory, there is nevertheless a need for a new and improved tendon anchor, including an anchor housing, a protuberance located substantially on the housing, a cut-out area located substantially on the housing and located substantially across from the protuberance, and a plurality of elongated tendon gripping projections located substantially adjacent to the protuberance and the cut-out area for substantially retaining the tendon within the tendon anchor.

It is a purpose of this invention to fulfill this and other needs in the art in a manner more apparent to the skilled artisan once given the following disclosure.

SUMMARY OF THE INVENTION

A feature of the present invention is a tendon anchor, including an anchor housing, a protuberance located substantially on the housing, a cut-out area located substantially on the housing and located substantially across from the protuberance, and a plurality of elongated tendon gripping projections located substantially adjacent to the protuberance and the cut-out area for substantially retaining the tendon within the tendon anchor.

Another feature of the present invention is the provision of a tendon anchor having at least one bone in-growth opening.

Another feature of the present invention is the provision of a tendon anchor having a plurality of openings in the anchor to accommodate the plurality of elongated tendon gripping projections.

Another feature of the present invention is the provision of a tendon anchor such that the housing has an inner diameter range of 3-12 mm.

Another feature of the present invention is the provision of a tendon anchor such that the cut-out area extends no further down than about 50% of the length of the tendon anchor.

Another feature of the present invention is t provision of a tendon anchor wherein the projections include teeth.

Another feature of the present invention is the provision of a tendon anchor such that the projections are oriented between 75 and 90 degrees with respect to the tendon anchor.

Another feature of the present invention is the provision of a tendon anchor having a hinge located at one end of the tendon anchor.

Another feature of the present invention is the provision of a tendon anchor being constructed of any suitable, durable, medical grade material such as poly-L-lactic acid (PLLA), titanium, steel, polyether ether ketone (PEEK), osteoconductive β-TCP (beta-TriCalcium Phosphate), or PLGA (poly (L-lactide co-glycolide) polymer or any combination of the aforementioned polymers.

Another feature of the present invention is the provision of a method for attaching a tendon to a bone, including the steps of: attaching a distal end of a tendon to a tendon anchor where the tendon anchor includes a protuberance and a cut-out area; creating a hole in the bone such that the hole in the bone is slightly larger than a diameter of the tendon anchor; applying pressure to the tendon anchor such that the tendon anchor enters into the bone at the hole created in the bone; and tilting the tendon anchor with tension from the tendon such that the protuberance contacts an undersurface of the bone and locks the tendon anchor under the bone and the tendon interacts with the cut-out area of the anchor.

Another feature of the present invention is the provision of a method for attaching a tendon to a bone including the step of employing elongated projections to retain the tendon substantially in the tendon anchor.

Another feature of the present invention is the provision of a method for attaching a tendon to a bone including the step of drilling a hole in the bone.

Another feature of the present invention is the provision of a method for attaching a tendon to a bone including the step of attaching one end of an insertion tool to the tendon anchor.

Another feature of the present invention is the provision of a method for attaching a tendon to a bone including the step of hammering the other end of the insertion tool to cause the tendon anchor to enter into the bone at the hole created in the bone.

Another feature of the present invention is the provision of a method for attaching a tendon to a bone including the step of removing the insertion tool after the tendon anchor protuberance has caught under the cortical bone.

Another feature of the present invention is a tendon anchor, including an anchor housing, a protuberance located substantially on the housing, a cut-out area located substantially on the housing and located substantially across from the protuberance, a plurality of elongated tendon gripping projections located substantially adjacent to the protuberance and the cut-out area for substantially retaining the tendon within the tendon anchor, and a hinge located at one end of the tendon anchor.

The preferred tendon anchor, according to various embodiments of the present invention, offers the following advantages: ease of use; a simple method for reattaching a tendon to bone; the tendon anchor can be simply malleted into the bone through a pre-drilled, appropriately sized hole; the tendon anchor permanently locks in the bone by tilting which is facilitated by pulling the tendon; the tendon anchor can be made out of poly-L-lactic acid (PLLA), titanium, steel, polyether ether ketone (PEEK), osteoconductive β-TCP (beta-TriCalcium Phosphate) or PLGA (poly (L-lactide, co-glycolide) polymer or any combination of the aforementioned polymers; the tendon anchor can be constructed in various sizes for a particular diameter of tendon (shoulder, hand, elbow); and the tendon anchor includes slotted holes for bony in-growth. In fact, in many of the preferred embodiments, these factors of ease of use, ease of malleting into the bone, ability to permanently lock in the bone by tilting, the use of poly-L-lactic acid (PLLA), titanium, steel, polyether ether ketone (PEEK), osteoconductive β-TCP (beta-TriCalcium Phosphate) or PLGA (poly (L-lactide, co-glycolide) polymer or any combination of the aforementioned polymers; varying the sizes of the tendon anchor, and the use of slotted holes for bony in-growth are optimized to an extent that is considerably higher than heretofore achieved in prior, known tendon anchors.

BRIEF DESCRIPTION OF DRAWINGS

The above mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which:

FIG. 20 is a front view of an alternate tendon anchor, prior to the tendon anchor being attached to the tendon, constructed in accordance with the present invention;

FIG. 21 is a front view of the alternate tendon anchor, with the tendon anchor being attached to the tendon, constructed in accordance with the present invention;

DETAILED DESCRIPTION OF PREFERRED EMBODIMENTS

Figure 1:
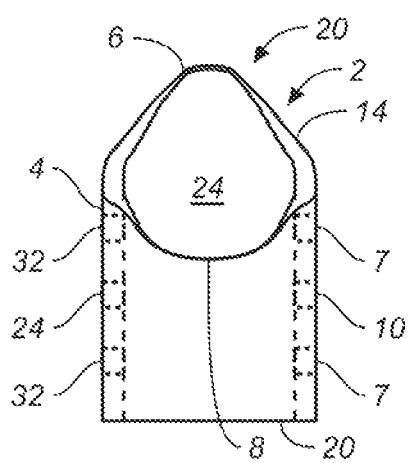
FIG. 1 is a front view of tendon anchor, constructed according to the present invention.
Figure 2:
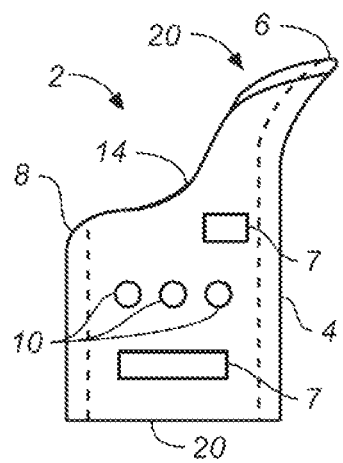
FIG. 2 is a side view of a tendon anchor, constructed according to the present invention.
Figure 3:
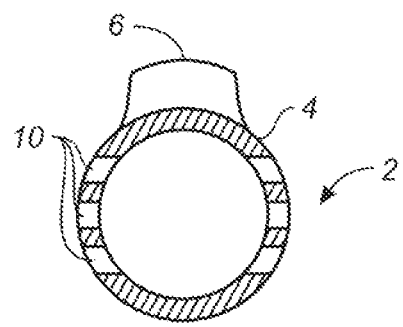
FIG. 3 is a top view of a tendon anchor, constructed according to the present invention.

Referring now to the drawings and more particularly to FIGS. 1-3, there is illustrated a tendon anchor 2, which is constructed in accordance with the present invention. As will be explained hereinafter in greater detail, the tendon anchor 2 is constructed to attach to a distal end of a tendon T and retain or anchor the tendon T within a hole H in an associated tendon bearing bone The advantages of tendon anchor 2 are ease of use, ease of malleting into the bone B, ability to permanently lock in the bone B by tilting, the use of poly-L-lactic acid (PLLA), titanium, steel, polyether ether ketone (PEEK), osteoconductive β-TCP (beta-TriCalcium Phosphate) or PLGA (poly (L-lactide, co-glycolide) polymer or any combination of the aforementioned polymers; varying the sizes of the tendon anchor, and providing a construction which facilitates for bony in-growth within the tendon anchor 2. A further advantage of the tendon anchor 2 is its ability to be utilized with, but not limited to, allograft tendons (posterior tibialis, anterior tibialis, palmaris longus, peroneal longus or brevis, biceps tendon) and autograft tendons or ruptured tendons including (posterior tibialis, anterior tibialis, palmaris longus, peroneal longus or brevis, long head biceps tendon, distal biceps tendon). Tendon anchor 2 can also be used for joint ligament reconstruction procedures such as the Tommy John Procedure, Lateral Ankle Ligament reconstruction, and patellofemoral stabilization procedures.

Considering now the tendon anchor 2 in greater detail with reference to FIGS. 1-3, the tendon anchor 2 generally comprises an open ended, hollow-like, cylindrically shaped housing 4 defined by a cylindrically-shaped side wail portion 14. A proximal portion of the side wall 14 is provided with a U-shaped cut-out area indicated generally at 8, which transposes at its proximal end into an outwardly extending protuberance 6 that flairs radially outwardly from the cylindrically shaped housing 4. The protuberance 6 is shaped so as to interact with the interior structure of a tendon anchoring bone B. The cut-out area 8 is shaped so as to interact with the tendon T. The cut-out area 8 and the protuberance 6 also cooperated to help define a tendon receiving opening 20 at the proximal end of the housing 4. The distal end of the housing 4 is provided with a generally circular shaped tendon exiting opening 22.

The interior surface 24 of the side wall 14 is generally a smooth polished surface that facilitates the free sliding of a tendon T in a friction-free manner within the interior of the housing 4 as a tendon T is pulled through the interior of the housing 4, as will be explained hereinafter in greater detail. The side wall 14 of the housing 4 is also provided with a right side set of generally circular shaped openings, such as an opening 10. The set of openings 10 are dimensioned for receiving therein a set of tendon engaging teeth 28 that cooperate with the housing 4 for helping to secure a tendon T within the hollow interior area of the housing 4. A corresponding left side set of openings, such as an opening 24 is provided opposed to the right side set of openings 10. The left side set of openings 24, like the right side set of openings, are also dimensioned for receiving therein another set of tendon engaging teeth 30 which also cooperate with the housing 4 for helping to secure a tendon T within the hollow interior area of the housing 4, as will be explained hereinafter in greater detail.

To facilitate bone in-growth with the housing 4, the side wall 14 is also provided with spaced apart bone in-growth windows indicated generally at 7 and 32, respectively. The set of spaced apart bone in-growth windows 7 and 32 are disposed substantially adjacent to openings 10 and 24.

Housing 4 is an open ended construction, preferably constructed of any suitable, durable, medical grade material such as poly-L-lactic acid (PLLA), titanium, steel, Polyether ether ketone (PEEK), osteoconductive β-TCP (beta-TriCalcium Phosphate) or PLGA (poly (L-lactide, co-glycolide) polymer or any combination of the aforementioned polymers. Housing 4, preferably, can be oval/ellipsoid or round at the opening on each end. Housing 4, preferably, has a height of between 10-18 mm, a thickness of between 5-10 mm, and inner diameter range of between 3-12 mm. However, it is to be understood that the dimensions of housing 4 can be varied in order to fit over different sizes and lengths of tendons.

Protuberance 6, preferably, is located along one side of housing 4 and is shaped so as to interact with the interior structure of the bone B (FIG. 15) to retain tendon anchor 2 within the bone B, as will be described in more detail later.

With respect to bone in-growth windows 7 and 32, these windows are conventionally formed in tendon anchor housing 4. Windows 7 and 32 are used to provide an area which interacts with the bone B (FIG. 15) so that bone deposits from the bone B enter into tendon anchor housing 4 at the bone in-growth windows 7 and 32, become calcified in tendon anchor housing 4, and allow tendon anchor housing 4 and tendon T to become substantially attached in a permanent-like manner to bone B.

With respect to cut-out area 8, cut-out area 8, preferably is formed in anchor 2 along a side wall 14 of housing 4 that is substantially opposite to protuberance 6. As will be discussed in more detail later, the location of the cut-out 8 with respect to the protuberance allows for tendon anchor 2 to be retained within the bone B when the tendon T (FIG. 4) pulls on tendon anchor 2. It is to be understood that cut-out area 8, preferably, should extend no further down than about 50% of the length of tendon anchor housing 4 so that tendon T can lay in tendon anchor housing 4 as the tendon anchor housing 4 tilts without constriction or sharp edges.

Regarding openings 10 and 24, openings 10 and 24 are conventionally created in housing 4 so that teeth 28 and 30 (FIG. 7) can be introduced into openings 10 and 24, respectively, to assist in retaining the tendon T within tendon anchor housing 4. Preferably, openings 10 and 24 have a diameter range of 0.5-3.0 mm.

Figures 4, 5, 6:
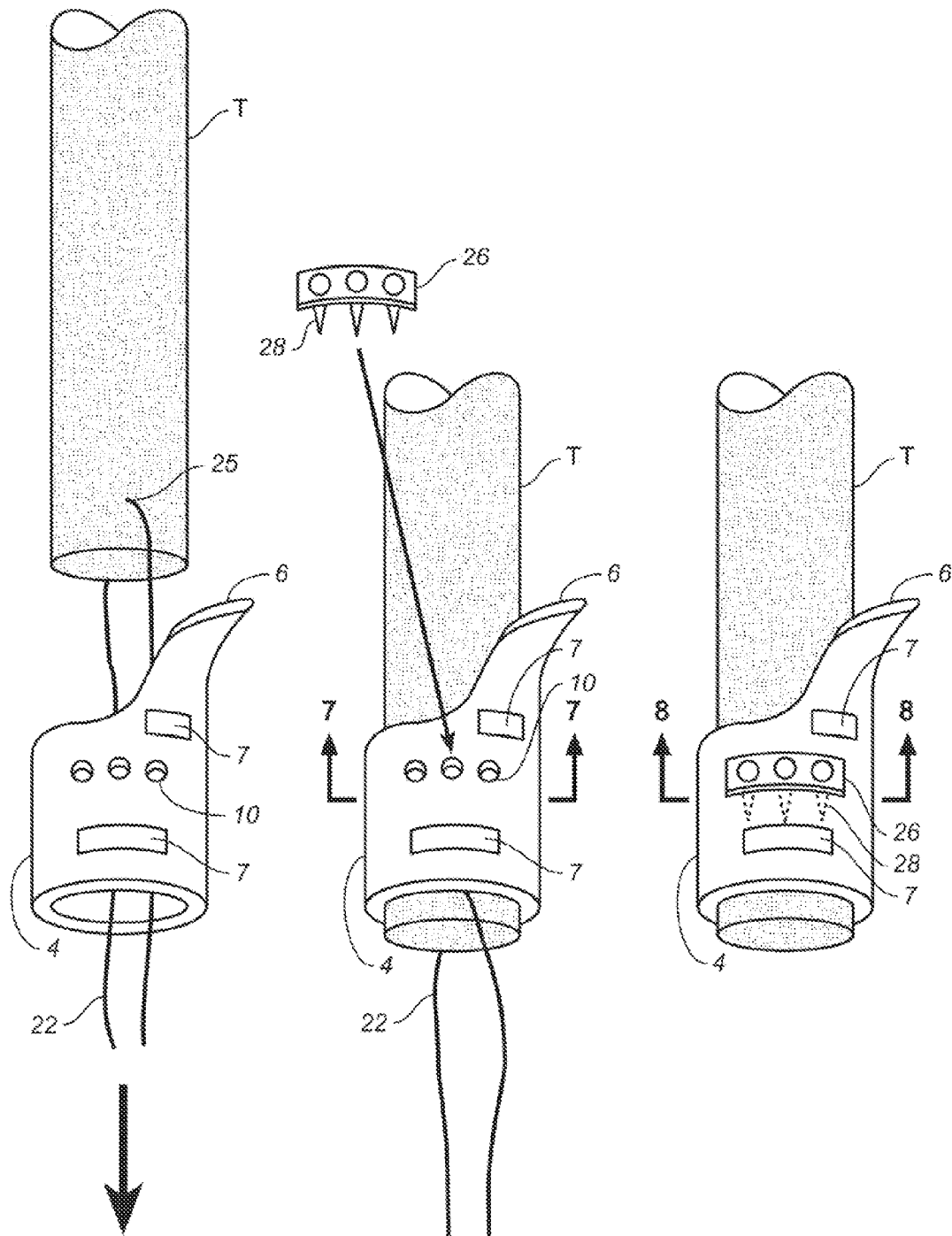
FIG. 4 is a schematic illustration of a distal end of a tendon being inserted into the tendon anchor, according to the present invention.
FIG. 5 is a schematic illustration of the distal end of the tendon being located in the tendon anchor, according to the present invention.
FIG. 6 is a schematic illustration of the distal end of the tendon being located in the tendon anchor and the retaining teeth being inserted into the tendon, according to the present invention.

With respect to FIGS. 4-6, there is illustrated an important feature of the present invention. In particular, FIGS. 4-6 illustrate a tendon T being inserted into tendon anchor housing 4 and the distal end of tendon T being retained within tendon anchor housing 4 through the use of a set of teeth 28 and 30.

As shown more clearly in FIG. 4, a distal end of tendon or tendon T is inserted into tendon anchor housing 4 through the use of conventional tendon insertion wires 22 which are connected to tendon T at 25.

Figure 7:
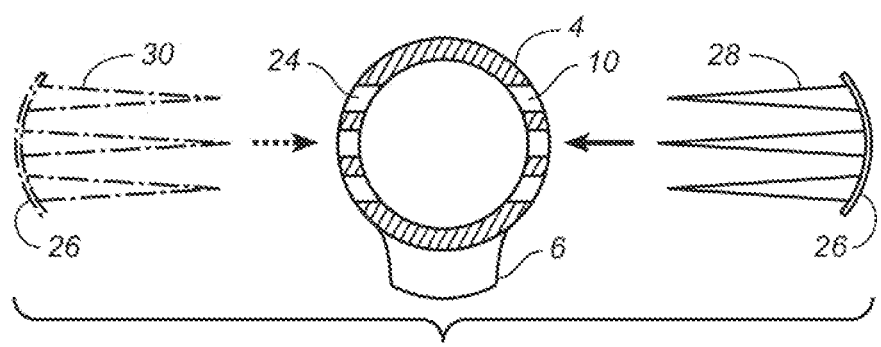
FIG. 7 is an exploded plan bottom sectional view of the tendon anchor, taken generally along line 2A-2A in FIG. 5, with the tendon removed for clarity.

Also as shown more clearly in FIGS. 5 and 7, to facilitate providing the tendon anchor housing 4 with a set of teeth 28, a pair of diametrically opposed tooth holders 26 having teeth 28 are inserted into openings 10. Preferably, tooth holders 26 and teeth 28 are constructed of any suitable, durable, medical grade material such as poly-L-lactic acid (PLLA), titanium, steel, polyether ether ketone (PEEK), osteoconductive .beta.-TCP (beta-TriCalcium Phosphate), or PLGA (poly (L-lactide, co-glycolide) polymer or any combination of the aforementioned polymers. It is to be understood that the size and shape of teeth 28 must be such that teeth 28 can engage tendon T and adequately retain the tendon T within tendon anchor housing 4. Finally, it is to be understood that teeth 28 can be oriented between 75 and 90 degrees with respect to the long axis of the tendon anchor housing 4.

FIG. 6 illustrates the diametrically opposed tooth holders 26 having teeth 28 inserted into openings 10 in tendon anchor housing 4 so as to retain the distal end of tendon T within tendon anchor housing 4.

With respect to FIGS. 7-10, there is illustrated another important feature of the present invention. In particular, FIGS. 7-10 show various sizes and arrangements of teeth 28 and 30.

Regarding FIG. 7, tendon anchor housing 4 and teeth 28 and 30 are illustrated in an exploded plan bottom sectional view of tendon anchor housing 4, taken generally along line 2A-2A in FIG. 5, with the tendon T removed for clarity An important feature of the invention shown in FIG. 7 is that teeth 28 and 30 can be located on both sides of tendon anchor housing 4. It is to be understood that anchor housing 4 can have any variable number of teeth 28 and 30 from 3 to 7 having varying lengths and, at possibly, varying angles between 75-90 degrees from the long axis of the tendon anchor housing 4.

Figure 8:
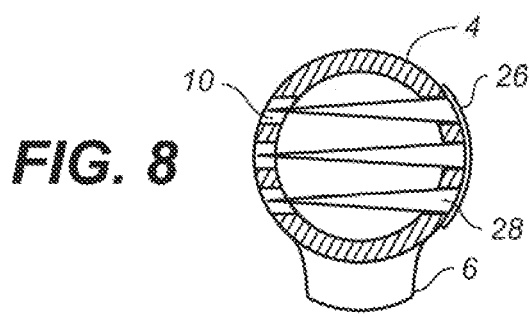
FIG. 8 is a cross-sectional view of the assembled tendon anchor, taken along line 2B-2B in FIG. 6, with the tendon removed for clarity.

With respect to FIG. 8, teeth 28 are sized so as to extend substantially across the entire inner diameter of tendon anchor housing 4. In this manner, only one set of teeth 28 are utilized to retain the tendon T (FIG. 6) within tendon anchor housing 4.

Figure 9:
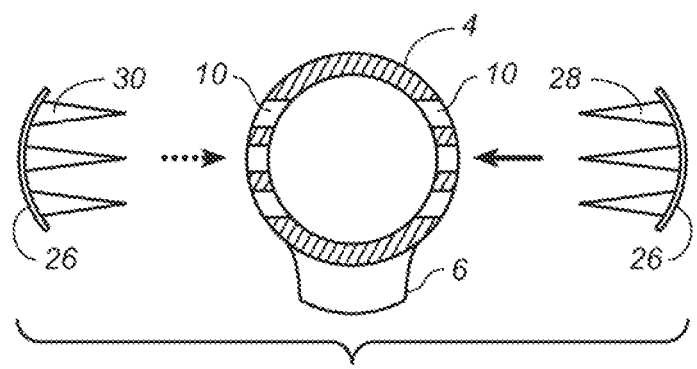
FIG. 9 is an exploded bottom plan sectional view of the tendon anchor, taken generally at 2B-2B in FIG. 6, showing an alternate tooth set environment wherein two opposed shorter sets of teeth occupy the insert holes, constructed in accordance with the present invention.

Regarding FIG. 9, tendon anchor housing 4 and teeth 28 and 30 are illustrated in an exploded bottom plan sectional view of tendon anchor housing 4, taken generally at 2A-2A in FIG. 5. As shown in FIG. 9, teeth 28 and 30 are to be utilized in retaining tendon T within tendon anchor housing 4.

Figure 10:
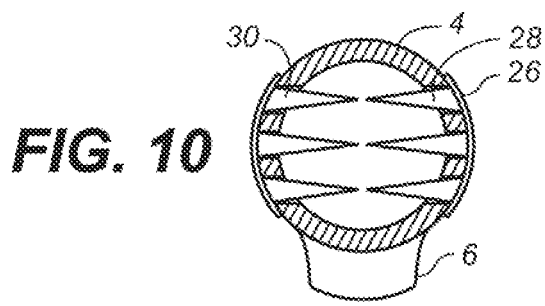
FIG. 10 is a cross-sectional view of the assembled tendon anchor wherein two sets of teeth are employed, constructed in accordance with the present invention.

With respect to FIG. 10, teeth 28 and 30 are sized so as to only extend partially across the inner diameter of tendon anchor housing 4. In this manner, teeth 28 and 30 are utilized to retain tendon T (FIG. 6) within tendon anchor housing 4.

Figure 11:
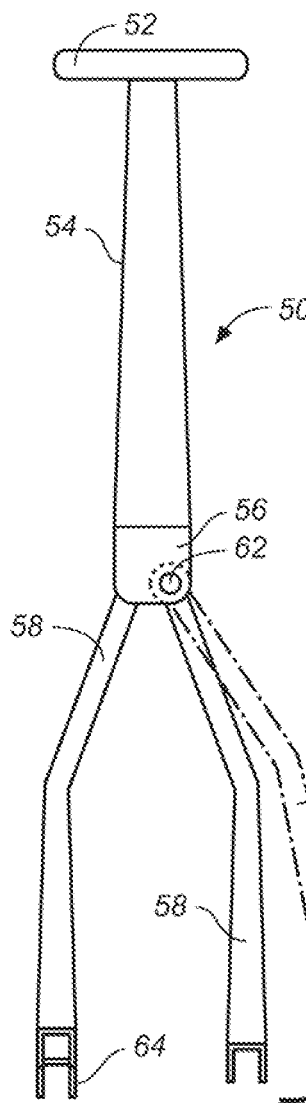
FIG. 11 is a front elevation view of an insertion tool that removably cooperates with the tendon anchor, according to the present invention.
Figure 12:
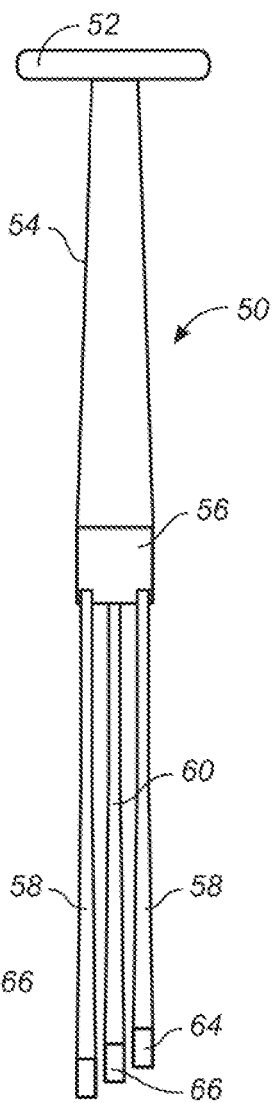
FIG. 12 is a left side view of the insertion tool shown in FIG. 12, constructed in accordance with the present invention.
Figure 13:
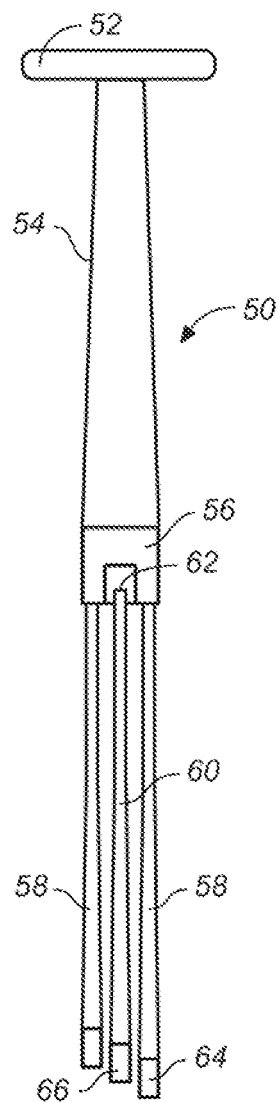
FIG. 13 is a right side view of the insertion tool n in FIG. 11, constructed in accordance with the present invention.
Figure 15:
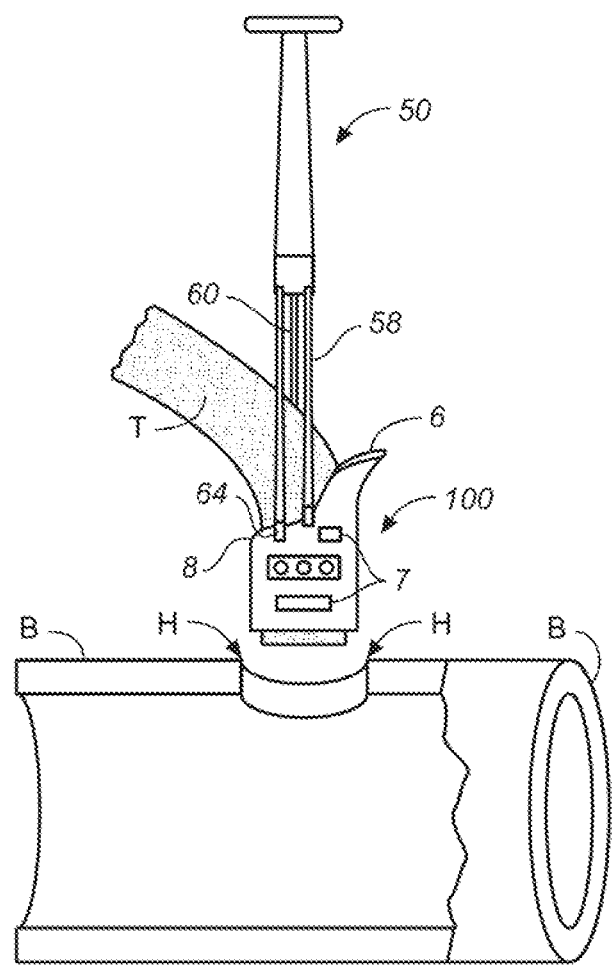
FIG. 15 is a schematic illustration of the tendon anchor attached to the tendon and the insertion tool attached to the tendon anchor, wherein the insertion tool is located substantially over the hole in the bone, in accordance with the present invention.

As shown more clearly in FIGS. 11-13, insertion tool 50 is illustrated. Insertion tool 50 is utilized to locate tendon anchor housing 4 which is attached to tendon T (FIG. 6) within the tendon associated bone B (FIG. 15). In this manner, insertion tool 50 allows for an easy insertion of tendon anchor housing 4 within the bone B while also allowing for easy removal of insertion tool 50 once tendon anchor housing 4 has been properly located within bone B.

With respect to FIG. 11, insertion tool 50 includes, in part, a handle 52, a handle extension 54, a bracket 56, stationary arms 58, a pivoting arm 60, a pivot 62, a stationary arm holder 64, and a pivoting arm holder 66. Insertion tool 50, preferably is constructed of any suitable, durable, medical grade material such as steel or titanium. As can be further seen in FIG. 11, the pivoting arm 60 pivots at a pivot, indicated generally at 62.

FIGS. 12 and 13 show left and right side views, respectively, of the insertion tool 50. A yet further important feature of the present invention is illustrated in FIGS. 12 and 13 in that the length of arms 58 and 60 are staggered to the provide a stable connection between insertion tool 50 and the tendon anchor housing 4 as the tendon anchor housing 4 is being inserted into the cortical bone B (FIG. 15).

With respect to FIGS. 14-19, there is illustrated another important feature of the present invention. In particular, FIGS. 14-19 illustrate the insertion of tendon anchor housing 4 into a hole H located in a cortical bone B, with the tendon anchor housing 4 being located within the hole H, the removal of the insertion tool 50, and the securing of tendon anchor housing 4 within cortical bone B. It is to be understood that prior to insertion of tendon T into tendon anchor housing 4, the diameter of tendon T is determined by conventional techniques. In this manner, the proper diameter of tendon anchor housing 4 can be employed.

Figure 14:
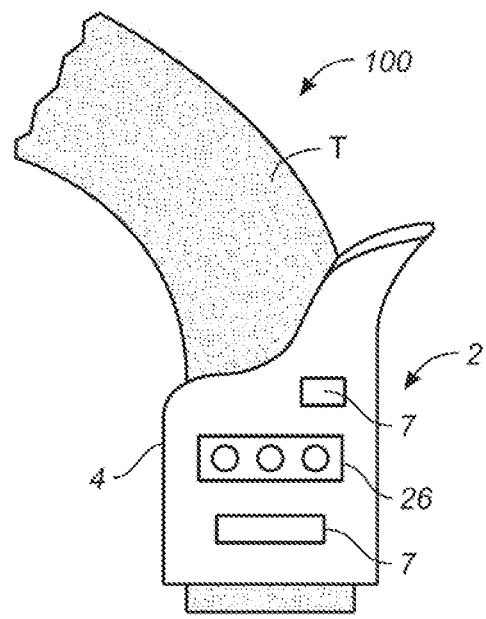
FIG. 14 is a schematic illustration of the tendon anchor attached to the tendon, prior to being inserted into a bone, according to the present invention.

As shown more, clearly in FIG. 14, tendon anchor assembly 100 is illustrated. The tendon anchor assembly 100 includes the tendon anchor housing 4, tendon T and diametrically opposed tooth holders 26 such that diametrically opposed tooth holders 26 have been inserted into tendon anchor housing 4 to retain tendon T within tendon anchor housing 4, as described earlier.

With respect to FIG. 15, insertion tool 50 is located along tendon anchor housing 4 of tendon anchor assembly 100 such that arm holders 64 contact portions of tendon anchor housing 4 adjacent to protuberance 6 and cut-out area 8. Also, insertion tool 50 is being utilized to locate tendon anchor assembly 100 substantially over the hole H that has been conventionally drilled in bone B.

Figure 16:
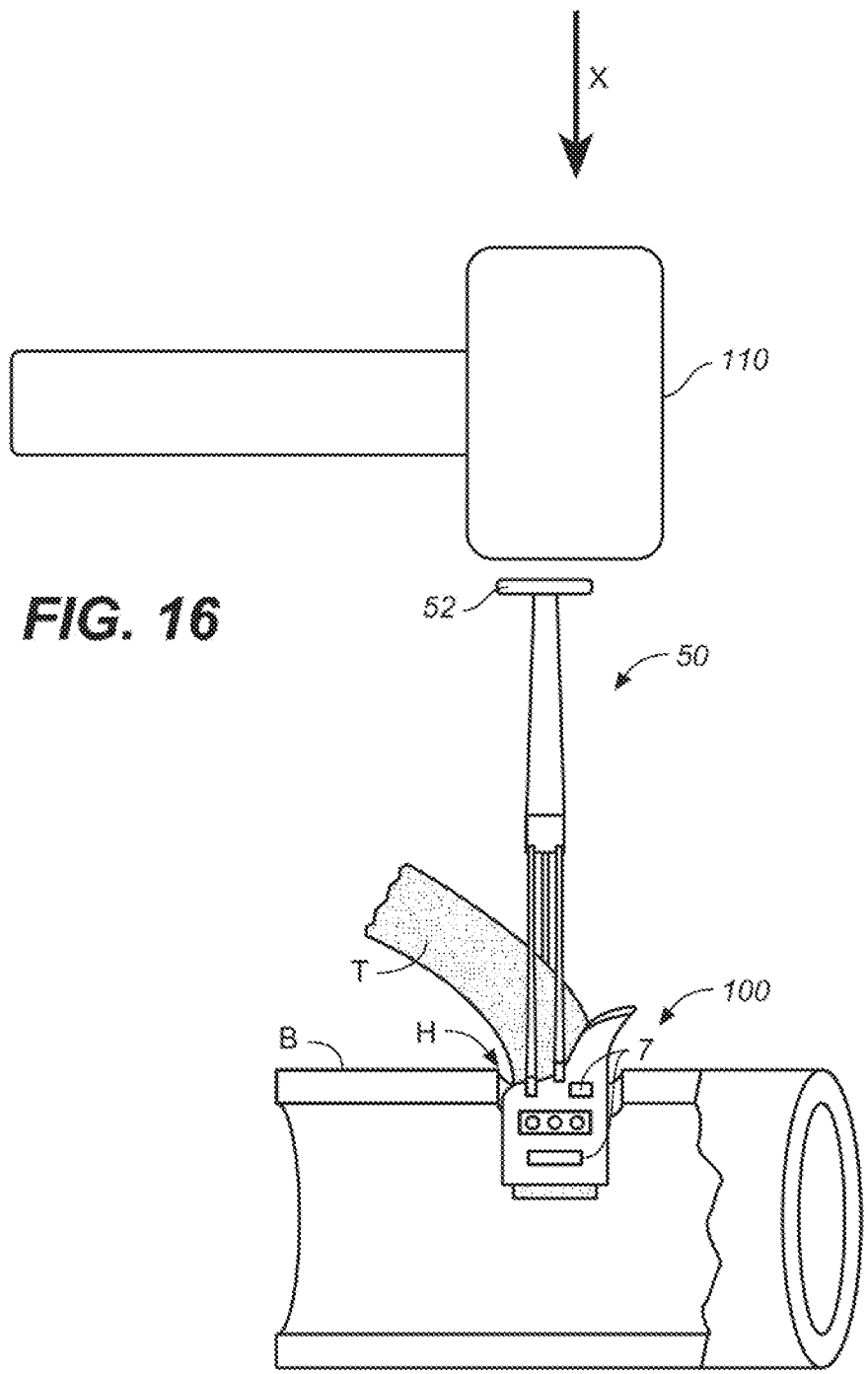
FIG. 16 is a schematic illustration of the tendon anchor attached to the tendon and the insertion tool attached to the tendon anchor, wherein the insertion tool is being lightly malleted to force the tendon anchor into the hole in the bone, in accordance with the present invention.

With respect to FIG. 16, a conventional mallet 110 is used to gently contact handle 52 of insertion tool 50 in order to force tendon anchor assembly 100 into hole H of cortical bone B along the direction of arrow (X).

Figure 17:
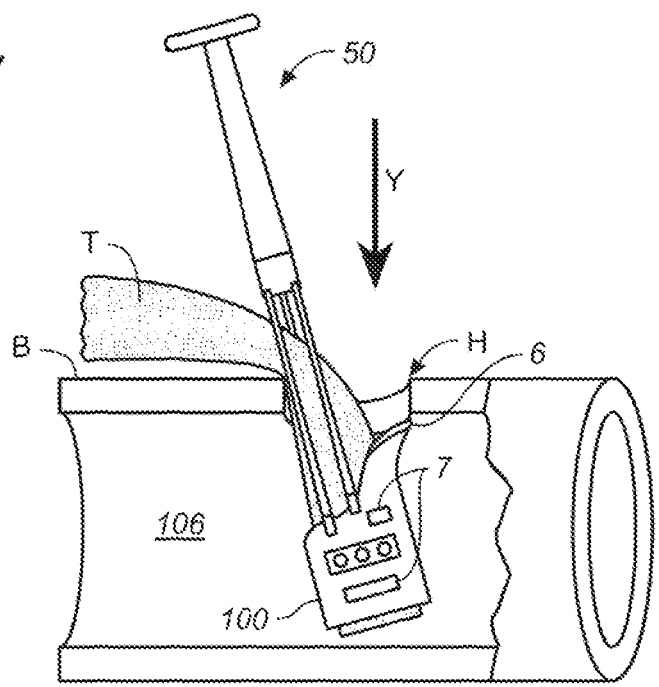
FIG. 17 is a schematic illustration of the tendon anchor attached to the tendon and the insertion tool attached to the tendon anchor, wherein the insertion tool is being pivoted in the hole in the bone, in accordance with the present invention.

As shown in FIG. 17, the application of mallet 110 forces tendon anchor assembly 100 along the direction of arrow (Y) such that tendon anchor assembly enters area 106 of bone B. Another important feature of the present invention is shown in FIG. 17 in that protuberance 6 is now located inside of bone B. In this manner, protuberance 6 is now able to interact with the interior of bone B, as will be described in greater detail later.

Figure 18:
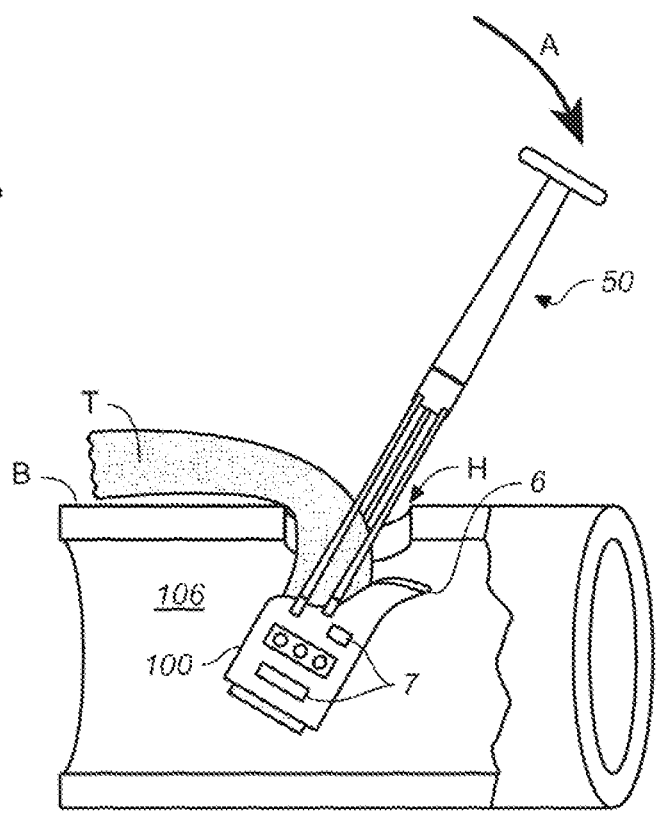
FIG. 18 is a schematic illustration of the tendon anchor attached to the tendon and the insertion tool attached to the tendon anchor, wherein the insertion tool is being pivoted in the hole in the bone so that the protuberance on the tendon anchor is located below the hole in the bone, in accordance with the present invention.

With respect to FIG. 18, insertion tool 50 is rotated along the direction of arrow (A) so that insertion tool 50 can be removed from tendon anchor assembly 100. Another important feature of the present invention is shown in FIG. 18 in that tendon T is now beginning pull on tendon anchor housing 4 and tendon T interacts with cut-out area 8 of tendon anchor housing 4.

Figure 19:
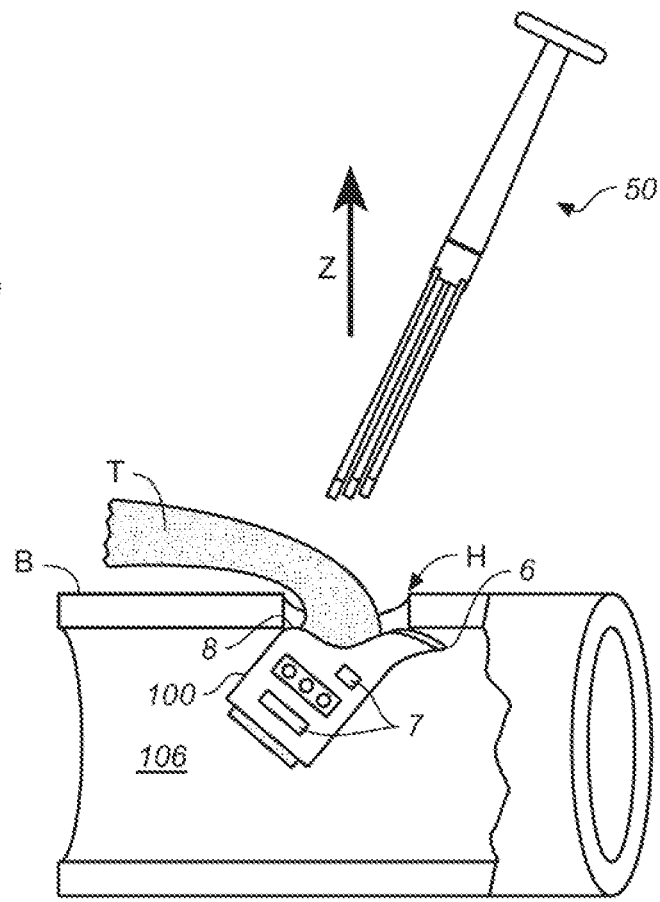
FIG. 19 is a schematic illustration of the insertion tool is being removed from the tendon anchor and the tendon being pulled such that the protuberance on the tendon anchor is now interacting with the bone to retain the anchor within the bone and the tendon interacts with the cut-out area, in accordance with the present invention.

With respect to FIG. 19, insertion tool 50 has been removed from tendon anchor assembly 100 along the direction of arrow (Z). Another important feature of the present invention is shown in FIG. 19 in that tendon T is now pulling on tendon anchor assembly 100 at the cut-out area 8 of tendon anchor housing 4 such that protuberance 6 interacts with the underside of bone B in order to retain tendon anchor assembly 100 within bone B.

Figure 22:
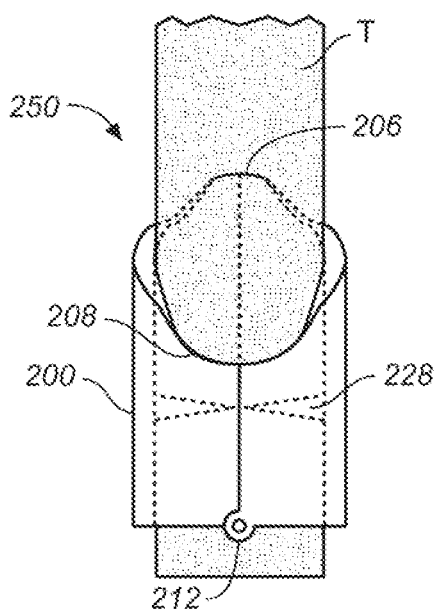
FIG. 22 is a front view of the alternate tendon anchor, with the tendon anchor attached to the tendon, constructed in accordance with the present invention.
Figure 23:
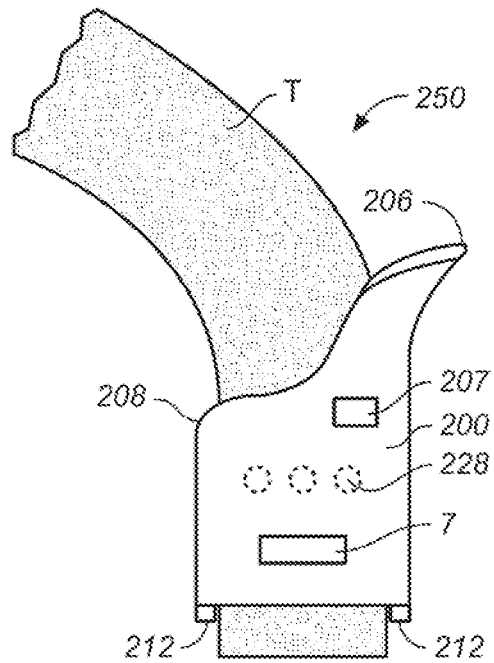
FIG. 23 is a side elevation of the alternate tendon anchor, with the tendon anchor attached to the tendon, constructed in accordance with the present invention.
Figure 24:
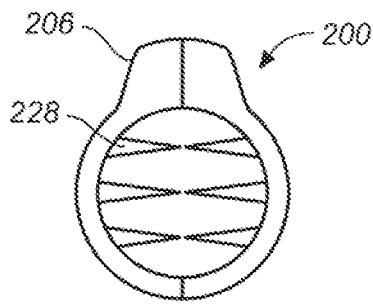
FIG. 24 is a top plan view of the alternate tendon anchor, with the tendon removed for clarity, constructed in accordance with the present invention.
Figure 25:
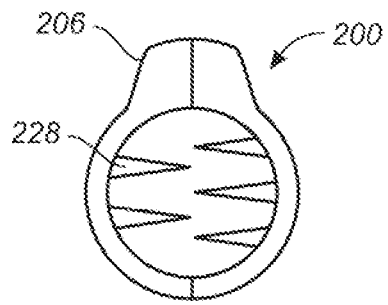
FIG. 25 is a top plan view of the alternate tendon anchor, with the tendon removed for clarity with an alternate arrangement of teeth, constructed according to the present invention.

With respect to FIGS. 20-25, there is illustrated another important feature of the present invention. In particular, FIG. 20 shows a hinged tendon anchor 200, prior to the tendon anchor 200 being attached to the tendon T with the hinge being located at one end of the tendon anchor 200. FIG. 21 shows the hinged tendon anchor 200 with the tendon anchor 200 being attached to the tendon T, as the hinged tendon anchor 200 pivots around pivot 212. FIG. 22 shows the hinged tendon anchor 200 with the tendon anchor attached to the tendon T, as the hinged tendon anchor 200 completes its rotation around hinge 212. FIG. 23 illustrates a side view of the hinged tendon anchor 200 with the tendon anchor 200 attached to the tendon T. FIGS. 24 and 25 show the hinged tendon anchor 200 with hinged tendon anchor 200 being completed closed and the tendon anchor 200 attached to the tendon T with alternate arrangements of teeth.

With respect to FIGS. 20-23, there is illustrated an alternate tendon anchor construction 200 having an open state as best seen in FIG. 20, a closing or tendon securing state as best seen in FIG. 21, and a closed state as best seen in FIG. 22. The tendon anchor 200 generally comprises an anchor housing 204, a protuberance 206, bone in-growth windows 207, a cut-out area 208, a set of openings 210, a hinge 212, and a set of teeth 228. It is to be understood that tendon anchor 200 is constructed of substantially the same materials as tendon anchor 2 (FIGS. 1-3). As further seen in FIG. 20, the distal end of tendon T is being inserted into tendon anchor housing 204 along the direction of arrow (X) in the same manner as the distal end of tendon T was inserted into tendon anchor housing 4, as shown in FIG. 4. However, in this embodiment, the distal end of tendon T is inserted into tendon anchor housing 204 while tendon anchor housing 204 is in its open state (FIG. 20).

With respect to FIG. 21, the pivoting of tendon anchor housing 204 around pivot 212 causes the closure of tendon anchor housing 204 along the direction of arrows (A and B). In this manner, teeth 228 begin to interact with the distal end of tendon T in order to retain tendon T within tendon anchor housing 204.

As shown in FIG. 22, the pivoting of tendon anchor housing 204 around pivot 212 is completed which causes the complete closure of tendon anchor housing 204. In this manner, the teeth 228 completely engage with the distal end of tendon T in order to retain tendon T within tendon anchor housing 204.

Considering now FIG. 23, a side view of tendon anchor housing 204 is illustrated. As clearly shown, a plurality of teeth 228 are utilized in tendon anchor housing 204 in order to adequately secure and retain a distal end portion of tendon T within tendon anchor housing 204. Tendon anchor housing 204 also includes protuberance 206, bone in-growth windows 207 and cut-out area 208 which function in the same manner as protuberance 6, bone in-growth window 7, and cut-out area 8 of tendon anchor housing 4, respectively, in FIGS. 1-3.

Regarding FIG. 24, there is illustrated a top view of tendon anchor housing 204 with teeth 228 being sized so as to only extend partially across the inner diameter of tendon anchor housing 204. In this manner, two set of teeth 228 are utilized to retain tendon T within tendon anchor housing 204.

With respect to FIG. 25, there is illustrated another embodiment in which teeth 228 are located in a staggered arrangement with respect to one another. In this manner, teeth 228 can interact with more surface area of the distal end portion of tendon T.

With respect to FIGS. 20-25, tendon anchor 200 can be used in the same manner as tendon anchor 2 in order to secure tendon 20 to bone 102, as shown in FIGS. 14-19. In particular, insertion tool 50 can also be applied to tendon anchor 200 in the same manner that insertion tool 50 was applied to tendon anchor 2 to insert tendon anchor 2 into bone 106.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim 1s not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising" "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein are a new and improved tendon anchor and a novel method of using the tendon anchor. The preferred tendon anchor, according to various embodiments of the present invention, offers the following advantages: ease of use; a simple method for reattaching a tendon to a bone; the tendon anchor can be simply malleted into the bone through a pre-drilled, appropriately sized hole; the tendon anchor permanently locks in the bone by tilting which is facilitated by pulling by the tendon; the tendon anchor can be made out of poly-L-lactic (PLLA), titanium, steel, Polyether ether ketone (PEEK), osteoconductive β-TCP (beta-TriCalcium Phosphate) or PLGA (poly (L-lactide, co-glycolide) polymer or any combination of the aforementioned polymers; the tendon anchor can be constructed in various sizes for a particular tendon (shoulder, hand, elbow); and the tendon anchor includes slotted holes for bony in-growth. In fact, in many of the preferred embodiments, these factors of ease of use, ease of malleting into the bone, ability to permanently lock in the bone by tilting, the use of poly-L-lactic acid (PLLA), titanium, steel, Polyether ether ketone (PEEK), osteoconductive β-TCP (beta-TriCalcium Phosphate) or PLGA (poly (L-lactide, co-glycolide) polymer or any combination of the aforementioned polymers; varying sizes of the tendon anchor, and the use of slotted holes for bony in-growth are optimized to an extent that is considerably higher than heretofore achieved in prior, known tendon anchors.

I claim:

1. A tendon anchor, comprising:
   a cylindrical tendon anchor housing sized and shaped to be inserted completely within a bone and attached to a tendon;
   a protuberance located on a first end of the cylindrical housing, wherein the protuberance flairs radially outward from the cylindrical housing;
   a cut-out area located on the first end of the cylindrical lousing and located across from the, protuberance; and
   a pair of diametrically opposed tooth holders insertable into the cylindrical housing wherein each tooth holder includes a plurality of elongated tendon gripping projections for insertion adjacent to the protuberance and the cut-out area, wherein the projections are, sized so as to extend partially across a hollow interior area of the cylindrical housing such that the projections cooperate with the cylindrical housing for helping to secure the tendon within the hollow interior area of the cylindrical housing.

2. The tendon anchor, as in claim 1 wherein the cylindrical housing is further comprised of at least one opening in the cylindrical housing to allow for bone in-growth.

3. The tendon anchor, as in claim 1, wherein the cylindrical housing is further comprised of: a plurality of openings in the cylindrical housing to accommodate the plurality of elongated tendon gripping projections.

4. The tendon anchor, as in claim 1, wherein the cylindrical using has an inner diameter range of 3-12 min.

5. The tendon anchor, as in claim 1, wherein the cut-out area extends no further down than about 50% of the length of the cylindrical housing.

6. The tendon anchor, as in claim 1, wherein the projections are further comprised of: teeth.

7. The tendon anchor, as in claim 1, wherein the projections are oriented between 75 and 90 degrees with respect to the cylindrical housing.

8. The tendon anchor, as in claim 1, wherein the cylindrical housing is further comprised of a hinge located at another end of the cylindrical housing.

9. The tendon anchor, as in claim 1, wherein the tendon anchor is constructed of any suitable, durable, medical grade material consisting of: poly-L-lactic acid (PLLA), titanium, steel, Polyether ether ketone (PEEK), osteoconductive beta-TCP (beta-TriCalcium Phosphate) or PLGA (poly (L-lactide, co-glycolide) polymer or any combination of the aforementioned polymers.

10. A tendon anchor, comprising:
    a cylindrical tendon anchor housing sized and shaped to the inserted completely within a bone and attached to a tendon;
    a protuberance located on a first end of the cylindrical housing, wherein the protuberance flairs radially outward from the cylindrical housing;
    a cut-out area located on the first end of the cylindrical housing and located across from the protuberance;
    a pair of diametrically opposed tooth holders insertable into the cylindrical housing wherein each tooth holder includes a plurality of elongated tendon, gripping projections for insertion adjacent to the protuberance and the cut-cut area, wherein the projections are sized so as to extend partially across a hollow interior area of the cylindrical housing such that the projections cooperate with the cylindrical housing for helping to secure the tendon within the hollow interior area of the cylindrical housing; and
    a hinge located at another end of the cylindrical housing.

11. The tendon anchor, as in claim 10, wherein the cylindrical housing is further comprised of: at least one opening in the housing to allow for bone in-growth.

12. Th tendon anchor, as in claim 10, wherein the cylindrical housing is further comprised of a plurality of openings in the cylindrical housing to accommodate the plurality of elongated tendon gripping projections.

13. The tendon anchor, as in claim 10, wherein the cutout area extends no further down than about 50% of the length of the cylindrical housing.

14. The tendon anchor, as in claim 10, wherein the projections are further comprised of: teeth.

15. A tendon anchor, comprising:
a cylindrical tendon anchor housing sized and shaped to be inserted completely within a bone and attached to a tendon, wherein the cylindrical housing is further comprised of at least one opening in the cylindrical housing to allow for bone in-growth;
a protuberance located on a first end of the cylindrical housing, wherein the protuberance flairs radially outward from the cylindrical housing:
a cut-out area located on the first end of the cylindrical housing and located across from the protuberance;
a pair of diametrically opposed tooth holders insertable into the cylindrical housing wherein each tooth holder includes a plurality of elongated tendon, gripping projections located adjacent to the protuberance and the cut-out area, wherein the projections are sized so as to extend partially across a hollow interior area of the cylindrical housing such that the projections cooperate with the cylindrical housing for helping to secure the tendon within the hollow interior area of the cylindrical housing; and
a hinge located at another end of the cylindrical housing.

16. The tendon anchor as in claim 15, wherein the cylindrical hocusing is further comprised of: a plurality of openings in the cylindrical housing to accommodate the plurality of elongated tendon gripping projections.

17. The tendon anchor, as in claim 15, wherein the cutout area extends no further down than about 50% of the length of the cylindrical housing.

18. The tendon anchor, as in claim 15, wherein the projections are further comprised of: teeth.

19. The tendon anchor, as in claim 15, wherein the cylindrical housing has an inner diameter range of 3-12 mm.

* * * * *